(12) United States Patent
Wang et al.

(10) Patent No.: US 11,426,327 B2
(45) Date of Patent: Aug. 30, 2022

(54) CONTROL SYSTEM FOR HAND-CONTROLLED PHYSIOTHERAPY EQUIPMENT AND ELECTRICAL STIMULATION MODE

(71) Applicants: Chien-Chi Wang, Taipei (TW); Szu-Cheng Sun, Taipei (TW)

(72) Inventors: Chien-Chi Wang, Taipei (TW); Szu-Cheng Sun, Taipei (TW)

( * ) Notice: Subject to any disclaimer, the term of this patent is extended or adjusted under 35 U.S.C. 154(b) by 587 days.

(21) Appl. No.: 15/990,980

(22) Filed: May 29, 2018

(65) Prior Publication Data
US 2021/0353498 A1 Nov. 18, 2021

(51) Int. Cl.
*A61H 39/00* (2006.01)
*A61N 1/04* (2006.01)

(52) U.S. Cl.
CPC ......... *A61H 39/002* (2013.01); *A61N 1/0472* (2013.01); *A61H 2201/5097* (2013.01)

(58) Field of Classification Search
CPC .................... A61N 1/0472; A61H 139/002
USPC ................................................ 607/2
See application file for complete search history.

*Primary Examiner* — Nadia A Mahmood
(74) *Attorney, Agent, or Firm* — Karin L. Williams; Mayer & Williams PC

(57) ABSTRACT

Hand-controlled physiotherapy equipment contains: a first electrode and a second electrode which are connected with living creatures so as to form a closed loop, an electrical stimulation system, a signal receiving unit, and a signal identification unit. The electrical stimulation system includes a sensing unit. The signal receiving unit is connected with the sensing unit in a wired manner or a wireless manner, the signal identification unit is configured to transform loop signals into time series signals, wherein when each of the time series signals has a specific interruption signal and a specific recovery signal, each time series signal triggers a mode adjustment signal in a control module. The control module includes a predetermined comparison database, and the comparison database has multiple set modes, wherein the multiple set modes respectively have multiple interruption signals and multiple recovery signals.

4 Claims, 7 Drawing Sheets

CONTROL SYSTEM FOR HAND-CONTROLLED PHYSIOTHERAPY EQUIPMENT AND ELECTRICAL STIMULATION MODE

This application is a Non-provisional of Provisional Application Ser. No. 62/512,820, filed May 31, 2017.

BACKGROUND OF THE INVENTION

Field of the Invention

The present invention relates to a control system for hand-controlled physiotherapy equipment and an electrical stimulation mode which produces loop signals so as to adjust the current mode.

Background of the Invention

Most people have reduced metabolic efficiency, immune function, low blood flow speed, incomplete digestion, slow endocrine because of their age, environmental and air pollution, busy life, idleness, overeating, thus lacking oxygen in organs, having slow metabolism of internal organs, and reducing detoxification to cause various chronic diseases, such as insane, migraine, and sore muscles. For traditional Chinese medicine, these chronic diseases happen due to unsmooth blood and they can be treated by clearing the body's meridians and having acupuncture to promote blood circulation.

Human body is a delicate and complex electric field, which can maintain the life phenomenon through the metabolism and regeneration of cells in the body. The metabolism involved in various cells is caused by the exchange of various mineral ions in the body and by potassium ions in the intracellular fluid and sodium ions in the external fluid. These processes are called "active potential", so people can maintain heath by balancing the potential.

Western medicine confirmed that when the human body is sick, the impedance of the surface of the skin at a certain point will drop, which coincides with the "hole" of Chinese medicine. There are about 730 acupuncture points throughout the body, and acupuncture treatment is the use of the "Salt-Bridge Principle" to achieve ion exchange by energizing two or more metals to each other so as to allow the cells in the body to become active, to stimulate the meridians, and to enable the body's physiological functions. Therefore, the electrotherapy device is acupuncture principle using traditional Chinese medicine to promote blood circulation, muscle contraction, analgesic, activated nerve function, bone rehabilitation, acupuncture massage.

Electrotherapy device is usually divided into several segments according to the intensity of the current, allowing users to adjust the number of segments. When the user turns on the current to form a closed loop by contacting the two electrode pieces, the current intensity will be transmitted to the user. When the user's body suddenly separates from the electrode pieces and contacts again, the body's skin feels uncomfortable due to stress. For example, when a physiotherapist uses a finger to perform a physical therapy for a patient through an electrotherapy device, in order to adjust the number of segments of the current intensity, the patient must be removed from the patient's body and turned to the console to adjust it and then re-adjust the patient.

When above-mentioned treatment takes long time, the patient will feel uncomfortable, because conducting current repeatedly.

The present invention has arisen to mitigate and/or obviate the afore-described disadvantages.

SUMMARY OF THE INVENTION

The primary aspect of the present invention is to provide a control system for hand-controlled physiotherapy equipment and an electrical stimulation mode by which the therapist sets the current mode by contacting the treated person with his/her finger, when treating the treated person so as to produce the loop signals and to trigger the mode adjustment signal, thus adjusting the current intensity or operation modes.

Another aspect of the present invention is to provide a method of applying the control system which is achieved by using application program so as to connect with the hand-controlled physiotherapy equipment in a wired or wireless manner or to directly connect with the hand-controlled physiotherapy equipment, thus adjusting the current intensity or operation modes when the therapist treats the treated person.

To obtain above-mentioned aspects, a control system for hand-controlled physiotherapy equipment and an electrical stimulation mode provided by the present invention contains: a first electrode, a second electrode, an electrical stimulation system, a signal receiving unit, and a signal identification unit.

The first electrode and the second electrode are connected with living creatures so as to form a closed loop.

The electrical stimulation system are arranged on the hand-controlled physiotherapy equipment, and the electrical stimulation system includes a sensing unit coupled with the electrical stimulation system so as to detect loop signals of the electrical stimulation system, wherein the electrical stimulation system is configured to connect with a first electrode and a second electrode.

The signal receiving unit is connected with the sensing unit in a wired manner or a wireless manner so as to receive the loop signals of the sensing unit.

The signal identification unit is configured to transform the loop signals into time series signals, wherein when each of the time series signals has a specific interruption signal and a specific recovery signal, each time series signal triggers a mode adjustment signal in a control module.

The control module is connected with an actuation module in the wired manner or the wireless manner, the control module includes a predetermined comparison database, and the comparison database has multiple set modes, wherein the multiple set modes respectively have multiple interruption signals and multiple recovery signals, when the specific interruption signal and the specific recovery signal of the mode adjustment signal are the same as one of the multiple interruption signals and one of the multiple recovery signals, a mode adjusting instruction is outputted to the actuation module, the actuation module is in connection with the electrical stimulation system in the wired manner or the wireless manner and switches the electrical stimulation system into a current output mode based on the mode adjusting instruction.

A method of applying the control system provided by the present invention contains steps of:

S1, detecting loop signals;

S2, transforming the loop signals into time series signals respectively;

S3 outputting a mode adjustment signal, wherein when each of the time series signals has a specific interruption signal and a specific recovery signal, each time series signal triggers the mode adjustment signal, wherein the specific interruption signal and the specific recovery signal present in each time series signal repeatedly and regularly;

S4, providing comparison database and executing comparison with the comparison database, wherein the comparison database has multiple set modes, and the multiple set modes respectively have multiple interruption signals and multiple recovery signals, when the specific interruption signal and the specific recovery signal of the mode adjustment signal are the same as multiple predetermined interruption signals and multiple predetermined recovery signals, a mode adjusting instruction is outputted;

S5, switching an electrical stimulation system to a current output mode based on the mode adjusting instruction, wherein the current adjustment element is configured to adjust a current intensity to a desired current mode or a desired intensity within a predetermined adjustment time based on the mode adjusting instruction.

DETAILED DESCRIPTION OF THE PREFERRED EMBODIMENTS

Figure 1:
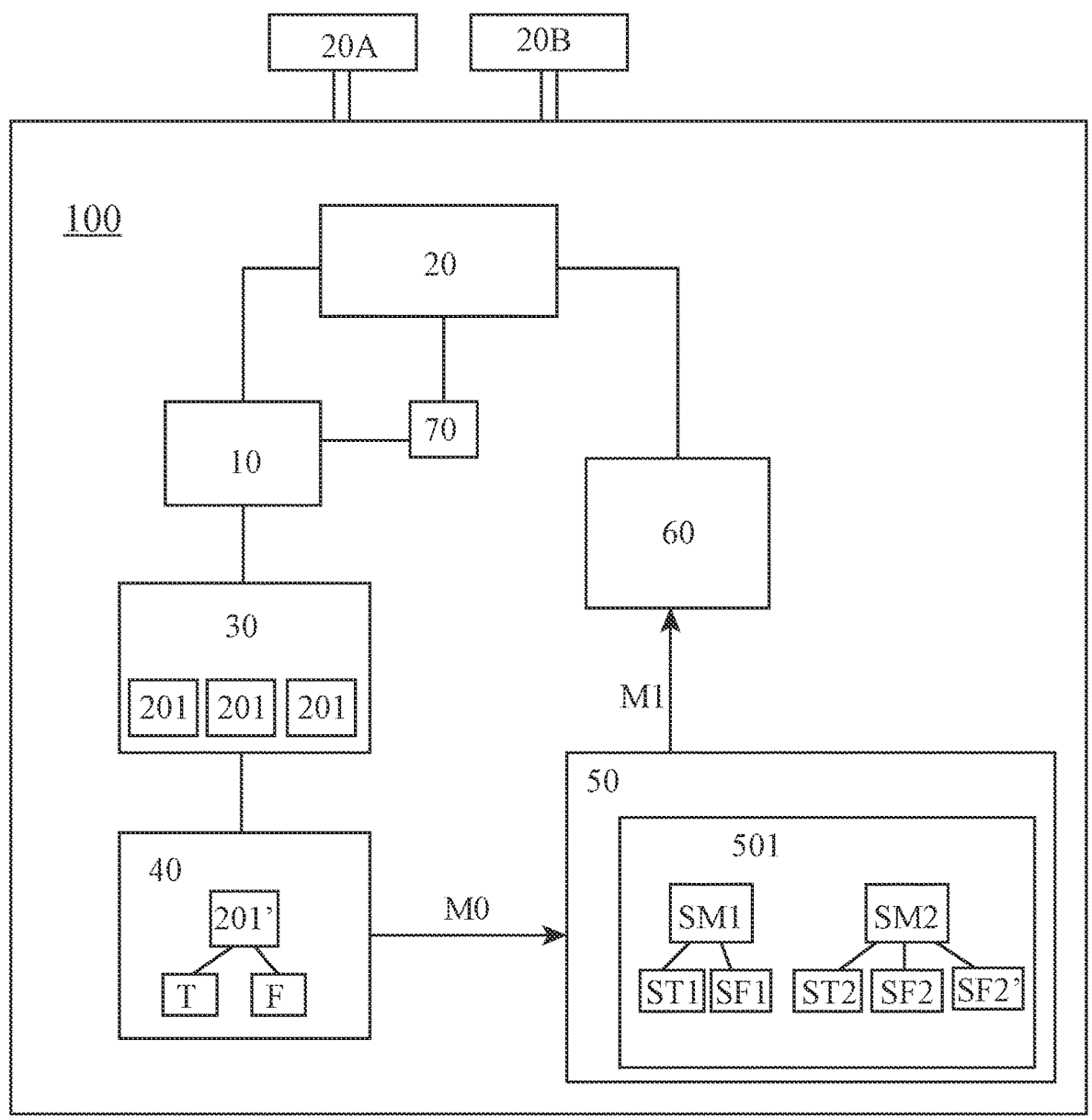
FIG. 1 is a schematic view of an electrical stimulation system according to a preferred embodiment of the present invention.

With reference to FIG. 1, hand-controlled physiotherapy equipment 100 according to a preferred embodiment of the present invention comprises: a first electrode 20A and a second electrode 20B which are connected with living creatures so as to form a closed loop. An electrical stimulation system 20 is arranged on the hand-controlled physiotherapy equipment 100, wherein a therapist is connected with the first electrode 20A, and a treated person is connected with the second electrode 20B, after starting the hand-controlled physiotherapy equipment 100, the therapist contacts with the treated person by using the electrical stimulation system 20 so that mirror electric current passes through the therapist and the treated person.

A sensing unit 10 is coupled with the electrical stimulation system 20 so as to detect loop signals 201 of the electrical stimulation system 20, wherein the loop signals 201 are current frequency signals after the first electrode 20A and the second electrode 20B are connected with the therapist and the treated person so as to form the closed loop; the loop signals 201 are interruption signals of conductive current among the first electrode 20A, the second electrode 20B, the therapist, and the treated person. The loop signals 201 are recovery signals, when the conductive current among the first electrode 20A, the second electrode 20B, the therapist, and the treated person are conducted after the interruption signals.

A signal receiving unit 30 is connected with the sensing unit in a wired manner or a wireless manner so as to receive the loop signals 201 of the sensing unit 10. In this embodiment, the wireless manner is applied by connecting gateways of a field or by connecting router(s) or relay terminal(s) of an internet. In another embodiment, the wireless manners is applied by using any one of global system for mobile communication (GSM), code division multiple access (CDMA), a Bluetooth, and ZigBee.

A signal identification unit 40 is configured to transform the loop signals 201 into time series signals 201', wherein when each of the time series signals 201' has a specific interruption signal T and a specific recovery signal F, each time series signal 201' triggers a mode adjustment signal M0 in a control module 50. The specific interruption signal T and the specific recovery signal F present in each time series signal 201' repeatedly and regularly.

Referring further to FIG. 1, the control module 50 is connected with an actuation module in the wired manner or the wireless manner, wherein the control module 50 includes a predetermined comparison database 50a, and the comparison database 501 has multiple set modes SM1, SM2, wherein the multiple set modes SM1, SM2 respectively have multiple interruption signals ST1, ST2 and multiple recovery signals SF1, SF2, SF2', when the specific interruption signal T and the specific recovery signal F of the mode adjustment signal M0 are the same as one of the multiple interruption signals ST1, ST2 and one of the multiple recovery signals SF1, SF2, a mode adjusting instruction M1 is outputted to the actuation module 60. The actuation module 60 is in connection with the electrical stimulation system 20 in the wired manner or the wireless manner and switches the electrical stimulation system 20 into a current output mode based on the mode adjusting instruction M1.

Figure 1A:
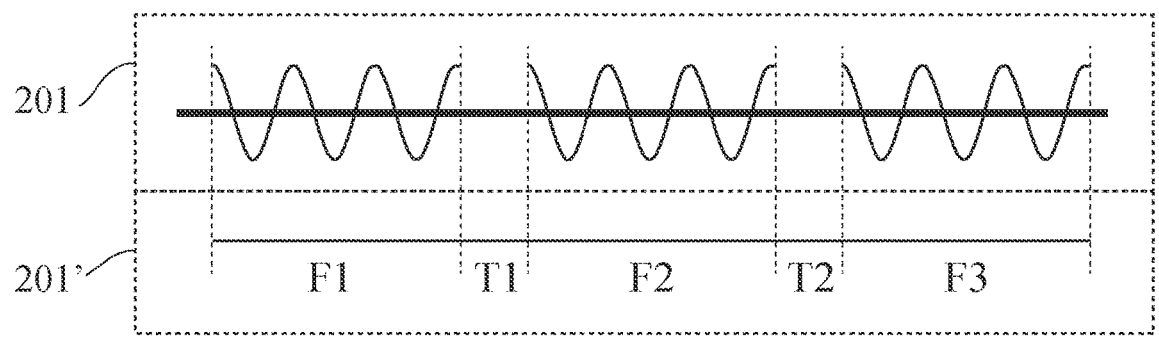
FIGS. 1A and 1B are a schematic view showing time series signals according to the preferred embodiment of the present invention.
Figure 1B:
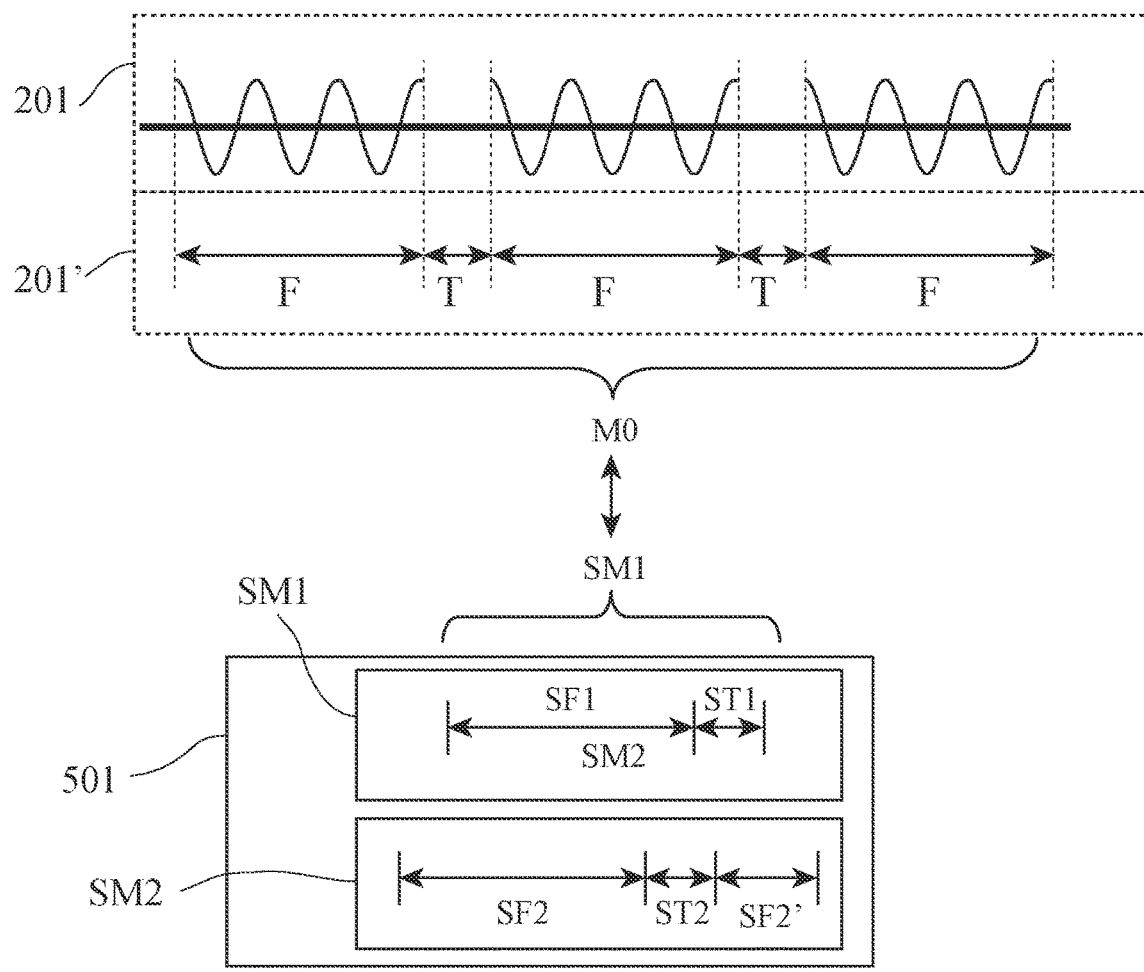

Each time series signal 201' captures multiple interruption signals T and multiple specific recovery signals F from the loop signals 201 in a time series arrangement manner. As shown in FIG. 1A, each time series signal 201' captures the multiple interruption signals T1, T2 and multiple recovery signals F1, F2, F3 from the loop signals 201 in the time series arrangement manner. As illustrated in FIG. 1B, when the multiple interruption signals T1, T2 have a same time length, and the multiple recovery signals F1, F2, F3 have the same time length, the multiple interruption signals T1, T2 are defined as the specific interruption signal T, and the multiple recovery signals F1, F2, F3 are defined as the specific recovery signal F. Thereafter, the specific interruption signal T and the specific recovery signal F are comprised with the multiple set modes SM1, SM2 of the comparison database 501. Taking a set mode SM1 for example, the set mode SM1 contains an interruption signal ST1 and a recovery signal SF1 which are respectively the same as the specific interruption signal T and the specific recovery signal F so as to output the mode adjusting instruction to the actuation module 60, and the actuation module 60 switches the electrical stimulation system 20 to the current output mode based on the mode adjusting instruction.

Figure 1C:
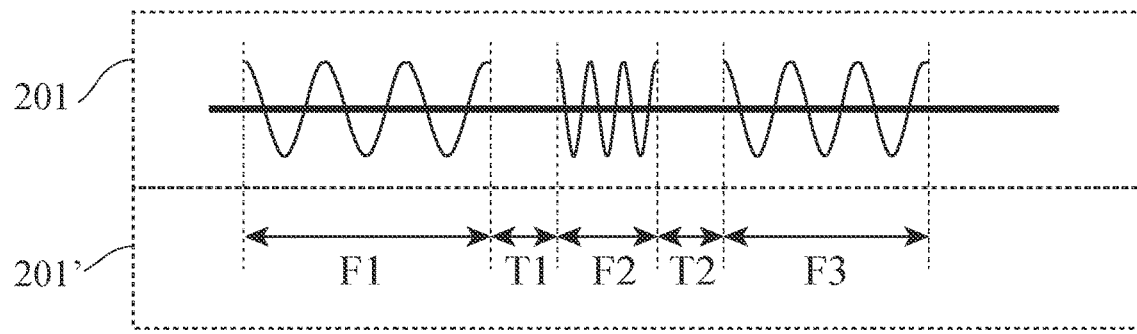
FIG. 1C is a schematic view showing time series signals according to another preferred embodiment of the present invention.

With reference to FIG. 1C, in another embodiment, each time series signal 201' captures multiple interruption signals T1, T2 and multiple recovery signals F1, F2, F3 from the loop signals 201 in the time series arrangement manner. As illustrated in FIG. 1B, when the multiple interruption signals T1, T2 do not have a same time length, and the multiple recovery signals F1, F2, F3 do not have the same time length, the signal identification unit 40 identifies that each time series signal does not trigger the mode adjustment signal.

Figure 1D:
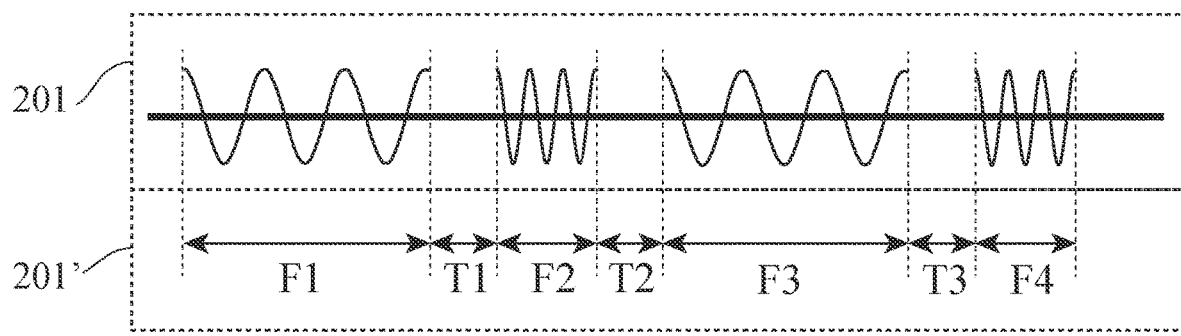
FIGS. 1D and 1E are a schematic view showing time series signals according to another preferred embodiment of the present invention.

With reference to FIG. 1D, in another embodiment, each time series signal 201' captures multiple interruption signals T1, T2, T3 and multiple recovery signals F1, F2, F3, F4 from the loop signals 201 in the time series arrangement manner, wherein the multiple interruption signals T1, T2, T3 have a same time length, some of the multiple recovery signals F1, F3 have a same time length, and the other recovery signals F2, F4 have another same time length.

Figure 1E:
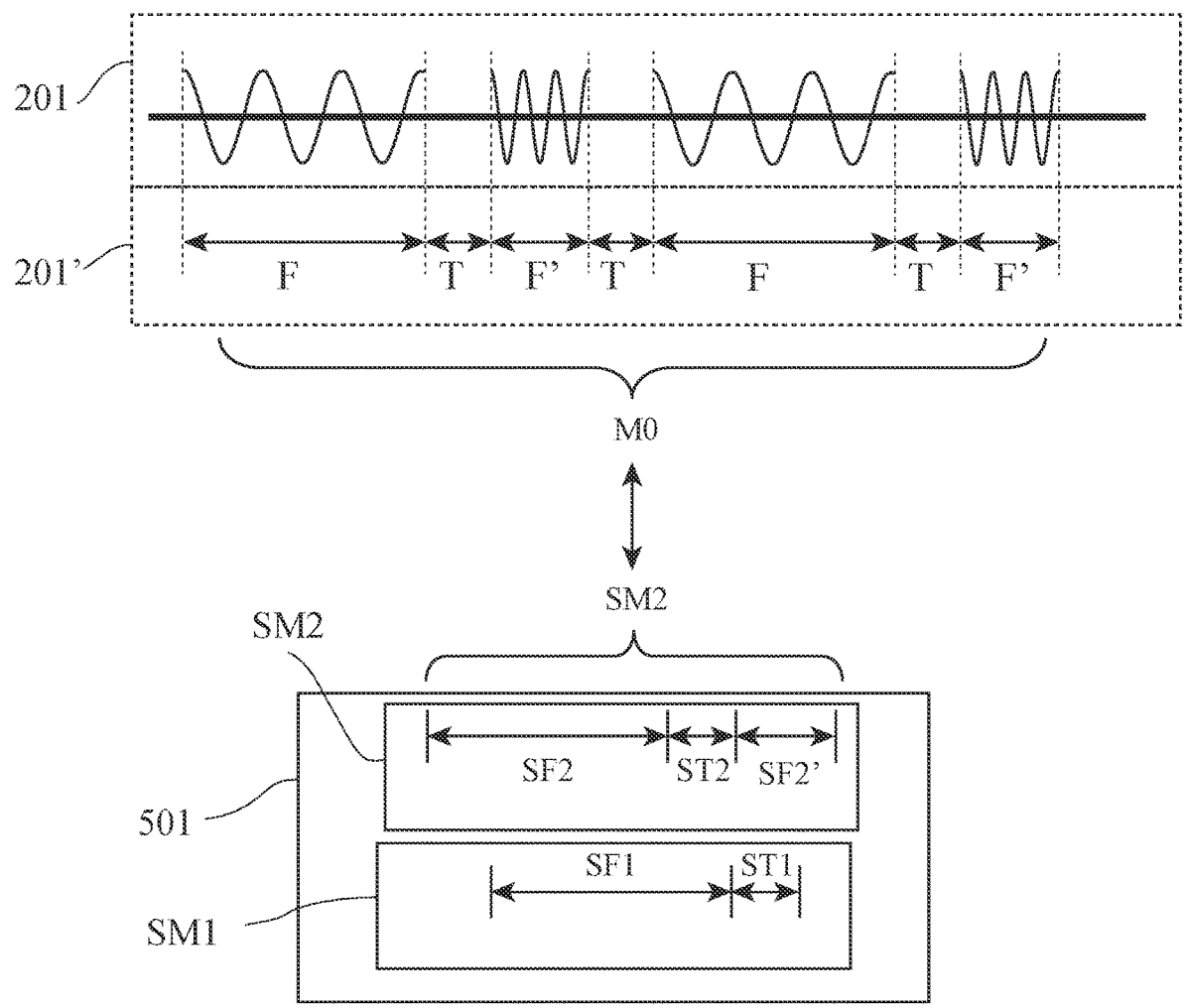

As illustrated in FIG. 1E, the multiple interruption signals T1, T2 are defined as the specific interruption signal T, recovery signals F1, F3 are defined as a first specific recovery signal F, and the other recovery signals F2, F4 are defined as a second specific recovery signal F'. Accordingly, a number of the multiple specific interruption signals T and the multiple specific recovery signals F are not limited as one, and each time series signal triggers the mode adjustment signal in the control module 50. As shown in FIG. 1E, the comparison database 501 has a set mode SM2, and the set mode has an interruption signal ST1 and recovery signals SF2, SF2', when the specific interruption signal T is identical to the specific recovery signals F, F', a mode adjusting instruction is outputted to the actuation module 60, and the actuation module 60 switches the electrical stimulation system 20 to the current output mode based on the mode adjusting instruction.

When therapist treats the treated person by way of the physiotherapy equipment 100 and changes output intensity (i.e., the current output mode) of the physiotherapy equipment 100, the therapist contacts with a hand of the treated person intermittently so as to form the loop signals 201. In the meantime, the signal identification unit 40 transforms the loop signals 201 into the time series signals 201', wherein when each time series signals has the specific interruption signal T and the specific recovery signal F, each time series signal 201' triggers the mode adjustment signal in the control module 50. Thereafter, the actuation module 60 switches the electrical stimulation system 20 to the current output mode or the current intensity, thus adjusting the output intensity of the electrical stimulation system 20 (i.e., adjusting the current intensity of the physiotherapy equipment 100) and switching operation modes.

The physiotherapy equipment 100 further comprises: a current adjustment element 70 connected with the electrical stimulation system 20 and the sensing unit 10 in the wired manner or the wireless manner so as to switch the electrical stimulation system 20 to a current mode or a current intensity based on the mode adjusting instruction M1 in a predetermined adjustment time.

Figure 2:
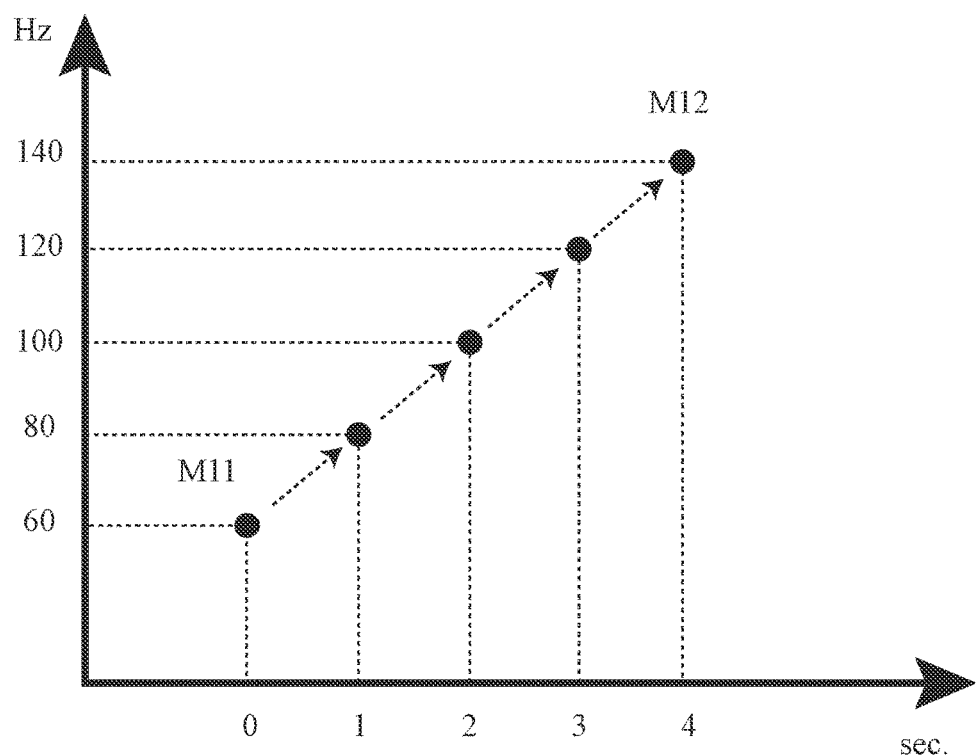
FIG. 2 is a schematic view showing the operation of the physiotherapy equipment according to the preferred embodiment of the present invention.

With reference to FIG. 2, the current adjustment element 70 adjusts the current mode, wherein a horizontal axis represents time, and vertical axis denotes a frequency value of the current. An original current output mode M11 is adjusted to a first current output mode M12, in the meantime, the frequency value of the current is adjusted within 60 Hz to 140 Hz, and the time is set within 0 to 4 seconds, wherein the frequency value of the current is adjustably increased to 20 Hz/per sec, thus adjusting the frequency value to 140 Hz in the first current output mode M12.

In this embodiment, the current adjustment element 70 is connected with the sensing unit 10 in the wired manner or the wireless manner so as to receive the loop signals 201. When the interruption signal received from the loop signals 201 within the predetermined adjustment time is over a set interruption time, and the recovery signals appear, the current adjustment element 70 reduces at least 10% of current intensity or current frequency signals. For example, when the therapist and the treated person connect with the first electrode 20A and the second electrode 20B individually after disconnecting the therapist and the treated person with the first electrode 20A and the second electrode 20B respectively, the therapist and the treated person feel uncomfortable. It is to be noted that the set interruption time is more than 1 second.

Figure 3:
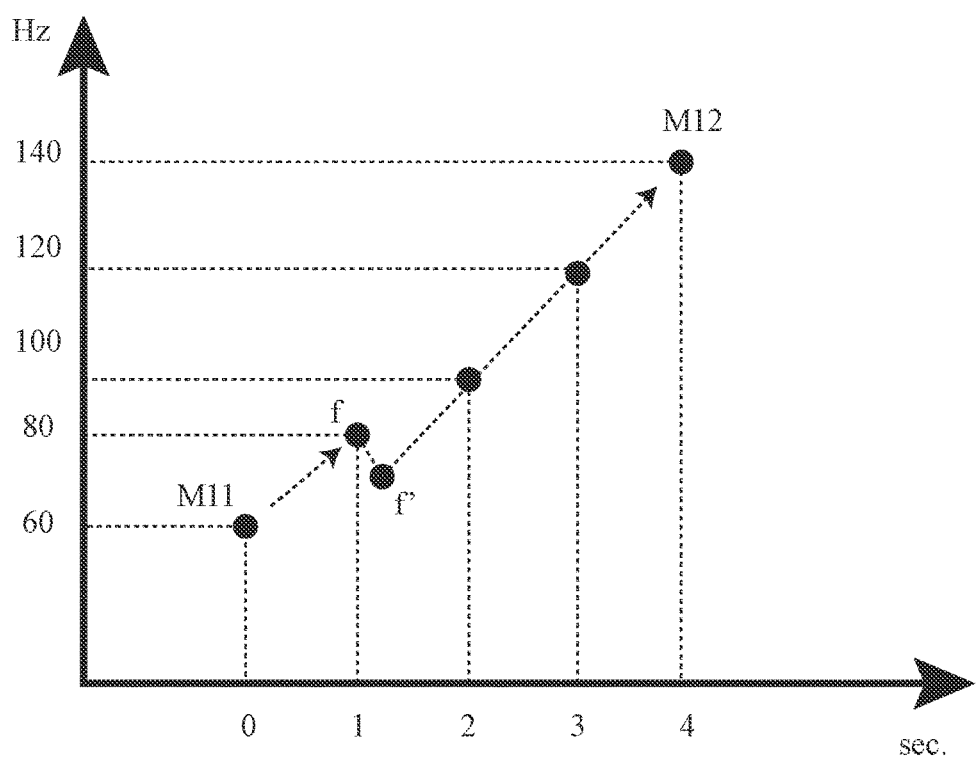
FIG. 3 is another schematic view showing the operation of the physiotherapy equipment according to the preferred embodiment of the present invention.

Referring to FIG. 3, in another embodiment, when the set interruption time is in 1st second, the frequency value of the current at a point f is 80 Hz. When the sensing unit 10 receives the interruption signal and the set interruption time is over one second, the recovery signal is not outputted at the frequency value of the current of 80 Hz but is outputted less than at least one 10% of 80 Hz, as denoted of a point f' in FIG. 3. It is to be noted that the recovery signal is adjustable according to genders, ages, physical sensitivities of the therapist and the treated person. For instance, when the therapist or/and the treated person have physical sensitivity (ies), the recovery signal is outputted at an original frequency value of the current of 30%. In contrast, the recovery signal is outputted at an original frequency value of the current of 10%.

Thereby, when the therapist treats the treated person, his/her hand contacts with the treaded person again after moving away from the treated person, the current adjustment element 70 adjustably decreases at least 10% of current so as to reduce discomfort of the treated person.

Figure 4:
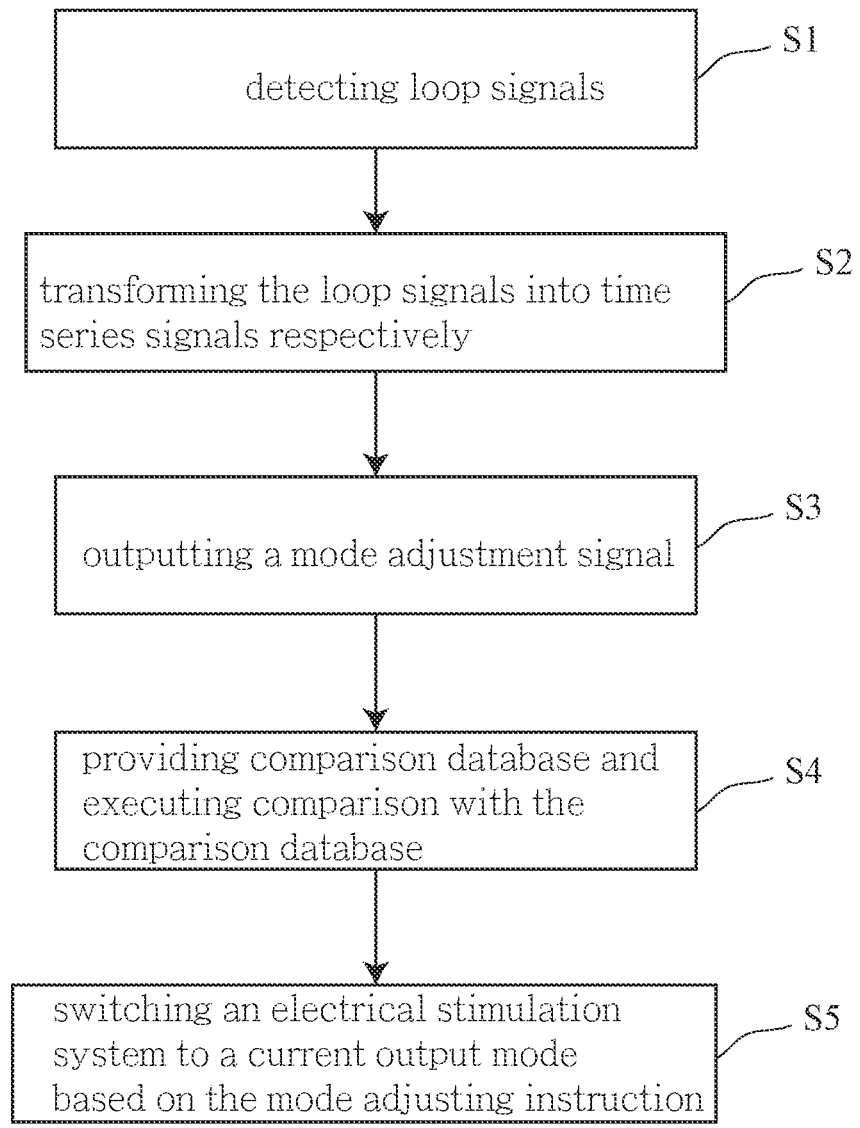
FIG. 4 is a flow chart showing a control system in an electrical stimulation mode according to the preferred embodiment of the present invention.

With reference to FIG. 4, a control system in an electrical stimulation mode according to the present invention is achieved by a third-party application program, wherein the control system is connected with the physiotherapy equipment in the wired manner or the wireless manner so as to switch using mode or current intensity mode.

A method of applying the control system for the hand-controlled physiotherapy equipment comprises steps of:

S1, detecting loop signals;

S2, transforming the loop signals into time series signals respectively;

S3 outputting a mode adjustment signal, wherein when each of the time series signals has a specific interruption signal and a specific recovery signal, each time series signal triggers the mode adjustment signal, wherein the specific interruption signal and the specific recovery signal present in each time series signal repeatedly and regularly;

S4, providing comparison database and executing comparison with the comparison database, wherein the comparison database has multiple set modes, and the multiple set modes respectively have multiple interruption signals and multiple recovery signals, when the specific interruption signal and the specific recovery signal of the mode adjustment signal are the same as multiple predetermined interruption signals and multiple predetermined recovery signals, a mode adjusting instruction is outputted;

S5, switching an electrical stimulation system to a current output mode based on the mode adjusting instruction, wherein the current adjustment element is configured to adjust a current intensity to a desired current mode or a desired intensity within a predetermined adjustment time based on the mode adjusting instruction. When the interruption signal of the each time series signal is over a set interruption time, the recovery signal appears so as to reduce at least 10% of current intensity. It is to be noted that the set interruption time is more than 1 second.

When the multiple interruption signals have a same time length, and the multiple recovery signals have the same time length, the multiple interruption signals are defined as the specific interruption signal, and the multiple recovery signals are defined as the specific recovery signal. When the multiple interruption signals do not have a same time length, and the multiple recovery signals do not have the same time length, each time series signal does not trigger the mode adjustment signal.

Figure 5:
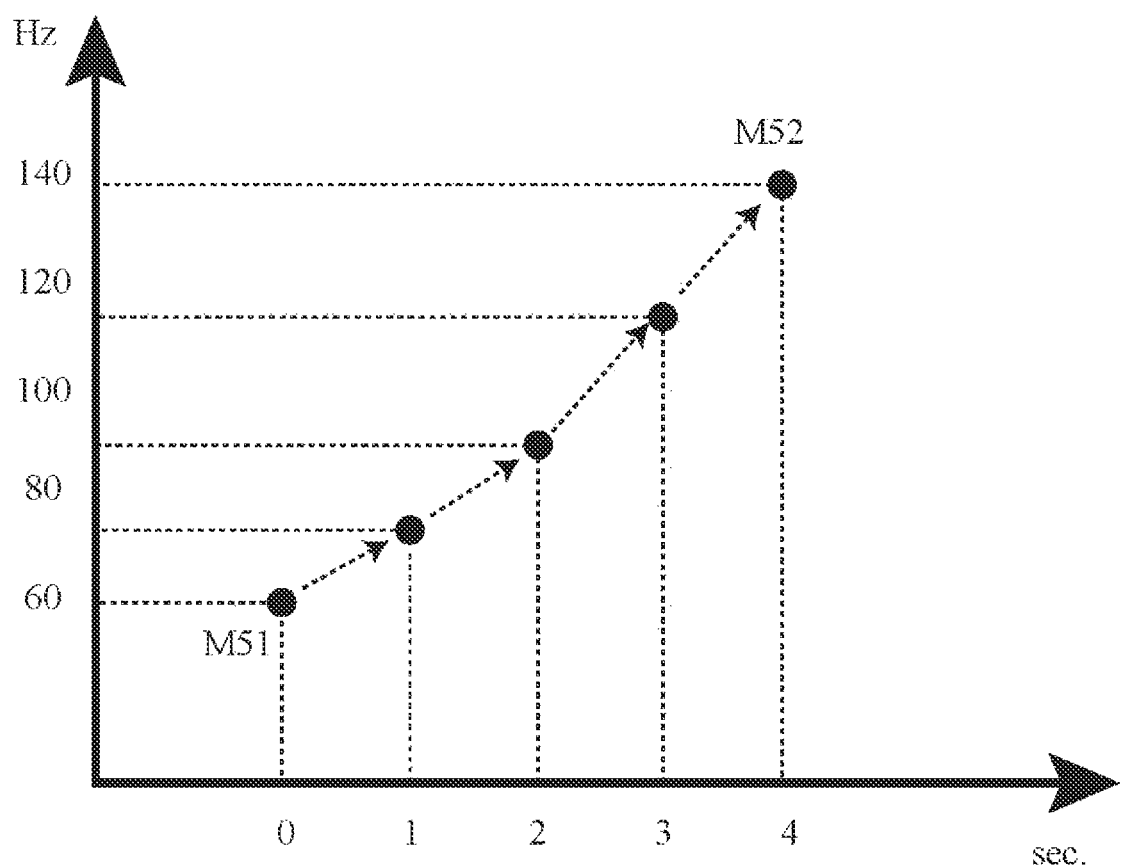
FIG. 5 is a schematic view showing the operation of the control system in the electrical stimulation mode according to the preferred embodiment of the present invention.

With reference to FIG. 5, in another embodiment, when a first mode M51 is adjusted to a second mode M25, the current output mode is executed based on the mode adjusting instruction. In this embodiment, the current intensity is adjusted to 140 Hz from 60 Hz, and the time is set to 4 seconds. The current intensity is increased from 60 Hz to 90 Hz within a first half of a predetermined adjustment time (such as in $1^{st}$ second to $2^{nd}$ second), and the current intensity is increased from 90 Hz to 140 Hz within the other half of the predetermined adjustment time (such as in $3^{rd}$ second to $4^{th}$ second). Accordingly, when the therapist contacts the treaded person after moving his/her hand away from the treated person over second, the current intensity is decreased so as to avoid discomfort of the treaded person.

Thereby, the control system control system in the electrical stimulation mode is achieved by the third-party application program, wherein the control system is connected with the physiotherapy equipment in the wired manner or the wireless manner so as to switch using mode or current intensity mode by contacting the treated person with the therapist' finger, thus producing the loop signals. In the meantime, the signal identification unit 40 transforms the loop signals 201 into the time series signals 201'. When each time series signals has the specific interruption signal T and the specific recovery signal F, each time series signal 201' triggers the mode adjustment signal in the control module. Thereafter, the actuation module 60 switches the electrical stimulation system 20 to the current output mode or current intensity, thus adjusting the current intensity of the physiotherapy equipment 100 and switching the operation modes.

While the preferred embodiments of the invention have been set forth for the purpose of disclosure, modifications of the disclosed embodiments of the invention and other embodiments thereof may occur to those skilled in the art. Accordingly, the appended claims are intended to cover all embodiments which do not depart from the spirit and scope of the invention.

What is claimed is:

1. Hand-controlled physiotherapy equipment comprising:
a first electrode and a second electrode;
an electrical stimulation system arranged on the hand-controlled physiotherapy equipment, and the electrical stimulation system including a sensing unit coupled with the electrical stimulation system so as to detect loop signals of the electrical stimulation system through the first electrode and the second electrode, wherein the electrical stimulation system is configured to connect with the first electrode and the second electrode;
a signal receiving unit connected with the sensing unit in a wired manner or a wireless manner so as to receive the loop signals of the sensing unit;
a signal identification unit configured to transform the loop signals into time series signals, wherein when each of the time series signals has a specific interruption signal and a specific recovery signal, each time series signal triggers a mode adjustment signal in a control module;
wherein the control module is connected with an actuation module in the wired manner or the wireless manner, the control module includes a predetermined comparison database, and the comparison database has multiple set modes, wherein the multiple set modes respectively have multiple interruption signals and multiple recovery signals, when the specific interruption signal and the specific recovery signal of the mode adjustment signal are the same as one of the multiple interruption signals and one of the multiple recovery signals, a mode adjusting instruction is outputted to the actuation module, the actuation module is in connection with the electrical stimulation system in the wired manner or the wireless manner and switches the electrical stimulation system into a current output mode based on the mode adjusting instruction.

2. The hand-controlled physiotherapy equipment as claimed in claim 1 further comprising a current adjustment element connected with the electrical stimulation system in the wired manner or the wireless manner so as to switch the electrical stimulation system to a current mode or a current intensity based on the mode adjusting instruction in a predetermined adjustment time.

3. The hand-controlled physiotherapy equipment as claimed in claim 1 further comprising a current adjustment element connected with the electrical stimulation system in the wired manner or the wireless manner so as to receive the loop signals of the electrical stimulation system, when the interruption signals received from the loop signals within the predetermined adjustment time is over a set interruption time, and the recovery signals appear, the current adjustment element reduces at least 10% of current intensity.

4. The hand-controlled physiotherapy equipment as claimed in claim 3, wherein the set interruption time is more than 1 second.

* * * * *